United States Patent [19]
Zurmühlen et al.

[11] Patent Number: 5,622,910
[45] Date of Patent: Apr. 22, 1997

[54] MIXTURES OF HERBICIDES AND ANTIDOTES

[75] Inventors: Frank Zurmühlen, Frankfurt am Main; Heinz-Josef Löher; Günter Schlegel, both of Liederbach; Rainer Schütze, Idstein; Klaus Bauer, Hanau; Hermann Bieringer, Eppstein, all of Germany

[73] Assignee: Hoechst Aktiengesellschaft, Frankfurt, Germany

[21] Appl. No.: 162,169

[22] PCT Filed: Jun. 26, 1992

[86] PCT No.: PCT/EP92/01445

§ 371 Date: Aug. 29, 1994

§ 102(e) Date: Aug. 29, 1994

[87] PCT Pub. No.: WO93/00010

PCT Pub. Date: Jan. 7, 1994

[30] Foreign Application Priority Data

Jun. 29, 1991 [DE] Germany .............. 41 21 663.6
Sep. 20, 1991 [DE] Germany .............. 41 31 334.8

[51] Int. Cl.$^6$ .............. A01N 25/32; A01N 43/54; A01N 43/66

[52] U.S. Cl. .............. 504/105; 504/106

[58] Field of Search .............. 504/105, 106

[56] References Cited

U.S. PATENT DOCUMENTS

| | | | |
|---|---|---|---|
| 4,639,266 | 1/1987 | Heubach et al. | 71/92 |
| 4,832,729 | 5/1989 | Shigematsu et al. | 71/92 |
| 4,881,966 | 11/1989 | Nyffeler et al. | 71/94 |
| 4,891,057 | 1/1990 | Sohn et al. | 71/72 |
| 4,902,340 | 2/1990 | Hubele | 71/94 |
| 4,931,087 | 6/1990 | Shigematsu et al. | 71/93 |
| 4,968,340 | 11/1990 | Kaku et al. | 71/92 |
| 4,969,949 | 11/1990 | Shigematsu et al. | 71/92 |
| 5,006,155 | 4/1991 | Rheinheimer et al. | 71/92 |
| 5,024,693 | 6/1991 | Gates et al. | 71/92 |
| 5,087,289 | 2/1992 | Kaku et al. | 71/93 |
| 5,380,852 | 1/1995 | Schütze et al. | 546/174 |

FOREIGN PATENT DOCUMENTS

| | | |
|---|---|---|
| 34951/89 | 11/1989 | Australia . |
| 0330990 | 9/1989 | European Pat. Off. . |
| 1-290671 | 5/1988 | Japan . |
| 89/1960 | 3/1989 | South Africa . |
| WO91/07874 | 6/1991 | WIPO . |
| WO91/08202 | 6/1991 | WIPO . |

*Primary Examiner*—S. Mark Clardy
*Attorney, Agent, or Firm*—Curtis, Morris & Safford, P.C.

[57] ABSTRACT

The invention relates to novel herbicidal agents which contain the herbicidal active substances from the group of the substituted pyrimidines and triazines and safener compounds of the formula B1 and/or B2,

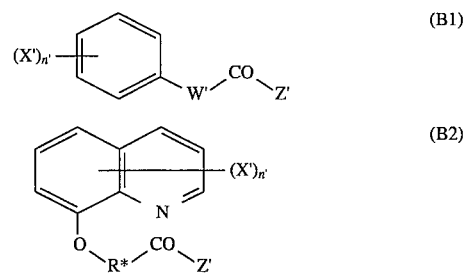

in which X' is hydrogen, halogen, (halo)alkyl, (halo)alkoxy or nitro, Z' is $OR^{31}$, $SR^{31}$ or $NR^{31}R$ or a heterocycle having at least one N atom and up to 3 hetero atoms, R' is an alkanediyl chain, n' is a number from 1 to 5, W' is a divalent heterocyclic radical, and the remaining radicals are as defined in the description. The invention furthermore relates to a method of protecting crop plants against phytotoxic secondary effects of herbicides, which comprises applying an effective amount of at least one compound of the formula B1 and/or B2 before, after or together with at least one herbicidal active substance from the group of the pyrimidines and triazines, to the plants, seeds of plants or the area under cultivation.

16 Claims, No Drawings

MIXTURES OF HERBICIDES AND ANTIDOTES

This application has been filed under 35 USC 371 from international application PCT/EP92/01445, filed Jun. 26, 1992.

The invention relates to the technical field of the crop protection agents, in particular active substance/antidote combinations which are outstandingly suitable for use against competing weeds in crops of useful plants.

Some of the more recently developed herbicidal active substances from the group of the substituted phenyl- or pyridyl-pyrimidinyl(triazinyl) ethers have very good properties and can be used at very low application rates against a broad range of grassy or broad-leaved weeds.

However, they are not completely compatible (selective) with some important crop plants such as corn or cereals, so that their use is greatly restricted. This is why they sometimes cannot be employed at all, or only at application rates which are too low to guarantee the desired broad herbicidal activity. For example, many herbicides of the substance class A) mentioned below cannot be employed selectively in corn or in cereals.

Recent experiments have shown, completely unexpectedly, that crop plants such as corn or wheat and barley can be protected against undesired damage due to the above-mentioned herbicides when they are applied together with certain compounds which act as herbicidal antidotes or safeners.

The invention therefore relates to herbicidal agents which contain

A) at least one herbicidal active substance from the group of the substituted pyrimidines and triazines of the formula A,

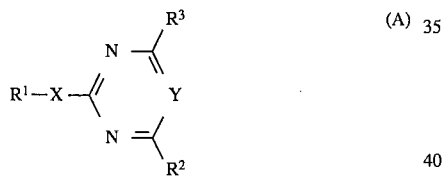

(A)

in which

X is O, S or $NR^4$,

Y is N or CH, $R^2$ and $R^3$ independently of one another are hydrogen, $(C_1-C_4)$alkyl, $(C_1-C_4)$haloalkyl, $(C_1-C_4)$alkoxy, $(C_1-C_4)$haloalkoxy, $(C_1-C_4)$alkylmercapto, $(C_1-C_4)$alkylamino or di$(C_1-C_4)$alkylamino, $R^1$ is a substituted aryl or heteroaryl radical of the formula

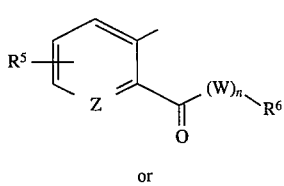

or

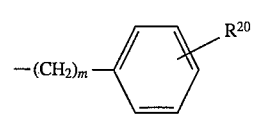

n is 0 or 1,

W is —O—, —$NR^4$—, —S—, —ON($R^{11}$)— or —O—N=C($R^{11}$)—,

Z is N, N→O or $CR^4$, $R^4$ and $R^5$ independently of one another are hydrogen, halogen, cyano, $(C_1-C_4)$alkyl, $(C_2-C_4)$alkenyl, $(C_2-C_4)$alkynyl, $(C_1-C_4)$alkoxy, $(C_2-C_4)$alkenyloxy, $(C_2-C_4)$alkynyloxy, benzyloxy, 4,6-di[$(C_1-C_4)$alkoxy]pyrimidin-2-yloxy, $(C_1-C_4)$alkylthio, $(C_2-C_4)$alkenylthio, $(C_2-C_4)$alkynylthio, benzylthio, $(C_1-C_4)$alkylamino, di-[$(C_1-C_4)$alkyl]amino, $(C_1-C_4)$haloalkyl or $(C_1-C_4)$haloalkoxy, $R^6$ is hydrogen, $(C_1-C_4)$alkyl, $(C_2-C_4)$alkenyl, $(C_2-C_4)$alkynyl, alkali metal or 1 equivalent alkaline earth metal, alkylammonium, aryl, $CF_3$ or $(CHR^{13})_{m'}CHR^7R^8$ where m' is 0 or 1, $R^7$ and $R^{13}$ independently of one another are hydrogen, $(C_1-C_4)$alkyl or $(C_1-C_4)$alkoxy, $R^8$ is $(C_1-C_4)$alkoxycarbonyl, cyano, halogen, acetyl, pivaloyl, benzoyl, $(C_1-C_4)$alkoxy, aryloxy, haloacetoxy, methanesulfonyloxy, hydroxyl, $(C_1-C_4)$alkylmercapto, $(C_1-C_4)$alkylsulfonyl, arylmercapto, di-$(C_1-C_4)$alkylamino, pyridyl, aryl or $CONR^9R^{10}$, $R^9$ and $R^{10}$ independently of one another are hydrogen, $(C_1-C_4)$alkyl, $(C_2-C_4)$alkenyl, aryl or benzyl, $R^{11}$ is hydrogen or $(C_1-C_4)$alkyl or $R^6$ and $R^{11}$ together are methylene, ethanediyl or propanediyl, $R^{12}$ is hydrogen, alkyl or alkoxy and aryl is phenyl or naphthyl, each of which is unsubstituted or mono- or disubstituted by radicals selected from the group comprising halogen, $(C_1-C_4)$alkyl, $(C_1-C_4)$alkoxy, phenoxy, nitro and $(C_1-C_4)$alkoxycarbonyl, or $R^1$ is a radical of the formula

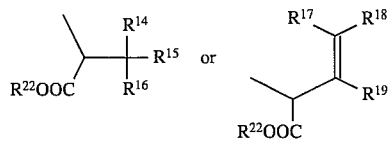

$R^{14}$ is hydrogen, halogen, halo $(C_1-C_4)$alkyl, $(C_1-C_4)$alkyl, cycloalkyl, $(C_1-C_4)$alkylmercapto$(C_1-C_4)$alkyl, hydroxy$(C_1-C_4)$alkyl, hydroxyl, cyano, aryloxy$(C_1-C_4)$alkyl, thienyl, aryl, dihydronaphthyl or

—(CH₂)ₘ—⌬—$R^{20}$ where aryl is as defined above, $R^{20}$ is hydrogen, halogen, nitro, $(C_1-C_4)$alkyl, $(C_1-C_4)$alkoxy or $S(O)_pR^{21}$, $R^{21}$ is alkyl, p is 0, 1 or 2, m is 0, 1 or 2, $R^{15}$ and $R^{16}$ independently of one another are hydrogen or alkyl, or together with the carbon atom form a 3-, 4-, 5- or 6-membered cycloalkane ring in which a methylene group can be replaced by oxygen and which can be substituted by one or two alkyl groups, $R^{17}$ and $R^{18}$ independently of one another are hydrogen or $(C_1-C_4)$alkyl, $R^{19}$ is $(C_1-C_4)$alkyl or phenyl, or $R^{18}$ and $R^{19}$ are —$(CH_2)_l$— where l is 3 or 4 and which can be substituted by one or two alkyl groups, $R^{22}$ is hydrogen, $(C_1-C_4)$alkyl, $(C_1-C_4)$alkenyl, $(C_1-C_4)$alkynyl, phenyl, $(C_1-C_4)$alkylideneamino, $(C_1-C_4)$alkoxycarbonyl$(C_1-C_4)$alkyl, $(C_1-C_4)$alkoxy$(C_1-C_4)$alkyl, halo$(C_1-C_4)$alkyl, cycloalkyl, nitro-substituted phenylmercapto$(C_1-C_4)$alkyl, halogen or benzyl which can be substituted by $(C_1-C_4)$alkyl or $(C_1-C_4)$alkoxy, or a salt thereof, and B) at least one compound from the group of the compounds of the formulae B1 and B2

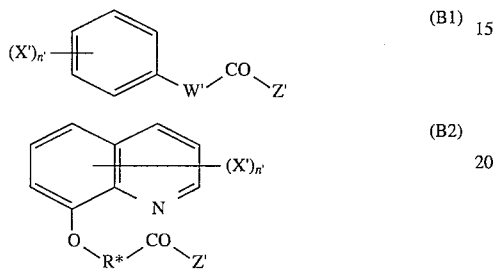

in which

X' is hydrogen, halogen, $(C_1-C_4)$alkyl, $(C_1-C_4)$alkoxy, nitro or $(C_1-C_4)$haloalkyl, Z' is $OR^{31}$, $SR^{31}$ or $NR^{31}R$, or forms a saturated or unsaturated 3- to 7-membered heterocycle which has at least one nitrogen atom and up to 3 hetero atoms, which is linked to the carbonyl group via the nitrogen atom and which is unsubstituted or substituted by radicals selected from the group comprising $(C_1-C_4)$alkyl, $(C_1-C_4)$alkoxy or optionally substituted phenyl, preferably a radical of the formula $OR^{31}$, $NHR^{31}$ or $N(CH_3)_2$, in particular of the formula $OR^{31}$, R is hydrogen, $(C_1-C_6)$alkyl, $(C_1-C_6)$alkoxy or optionally substituted phenyl, R* is a ($C_1$ or $C_2$)alkanediyl chain which can additionally be substituted by one or two $(C_1-C_4)$alkyl radicals, preferably —$CH_2$—, $R^{31}$ is hydrogen, $(C_1-C_{18})$alkyl, $(C_3-C_{12})$cycloalkyl, $(C_2-C_8)$alkenyl or $(C_2-C_8)$alkynyl, where the above carbon-containing radicals are unsubstituted or mono- or polysubstituted, preferably up to trisubstituted, by identical or different radicals selected from the group comprising halogen, hydroxyl, $(C_1-C_8)$alkoxy, $(C_1-C_8)$alkylmercapto, $(C_2-C_8)$alkenylmercapto, $(C_2-C_8)$alkynylmercapto, $(C_2-C_8)$alkenyloxy, $(C_2-C_8)$alkynyloxy, $(C_3-C_7)$cycloalkyl, $(C_3-C_7)$cycloalkoxy, cyano, mono- and di$(C_1-C_4)$alkylamino, $(C_1-C_8)$alkoxycarbonyl, $(C_2-C_8)$alkenyloxycarbonyl, $(C_1-C_8)$alkylmercaptocarbonyl, $(C_2-C_8)$alkynyloxycarbonyl, $(C_1-C_8)$alkylcarbonyl, $(C_2-C_8)$alkenylcarbonyl, $(C_2-C_8)$alkynylcarbonyl, 1-(hydroxyimino)$(C_1-C_6)$alkyl, 1-[$(C_1-C_4)$alkylimino]$(C_1-C_4)$alkyl, 1-[$(C_1-C_4)$alkoxyimino]$(C_1-C_6)$alkyl, $(C_1-C_8)$alkylcarbonylamino, $(C_2-C_8)$alkenylcarbonylamino, $(C_2-C_8)$alkynylcarbonylamino, aminocarbonyl, $(C_1-C_8)$alkylaminocarbonyl, di-$(C_1-C_6)$alkylaminocarbonyl, $(C_2-C_6)$alkenylaminocarbonyl, $(C_2-C_6)$alkynylaminocarbonyl, $(C_1-C_8)$alkoxycarbonylamino, $(C_1-C_8)$alkylaminocarbonylamino, $(C_1-C_6)$alkylcarbonyloxy which is unsubstituted or substituted by halogen, nitro, $(C_1-C_4)$alkoxy or optionally substituted phenyl, or $(C_2-C_6)$alkenylcarbonyloxy, $(C_2-C_6)$alkynylcarbonyloxy, $(C_1-C_8)$alkylsulfonyl, phenyl, phenyl$(C_1-C_6)$alkoxy, phenyl$(C_1-C_6)$alkoxycarbonyl, phenoxy, phenoxy$(C_1-C_6)$alkoxy, phenoxy$(C_1-C_6)$alkoxycarbonyl, phenylcarbonyloxy, phenylcarbonylamino, phenyl$(C_1-C_6)$alkylcarbonylamino, the last 9 radicals mentioned being unsubstituted in the phenyl ring or mono- or polysubstituted, preferably up to trisubstituted, by identical or different radicals selected from the group comprising halogen, $(C_1-C_4)$alkyl, $(C_1-C_4)$alkoxy, $(C_1-C_4)$haloalkyl, $(C_1-C_4)$haloalkoxy and nitro, and radicals of the formulae —$SiR'_3$, —O—$SiR'_3$, $R'_3Si(C_1-C_8)$alkoxy, —CO—O—$NR'_2$, —O—N=$CR'_2$, —N=$CR'_2$, —O—$NR'_2$—$CH(OR')_2$ and —O—$(CH_2)_m$—$CH(OR')_2$, where the R' radicals in said formulae independently of one another are hydrogen, $(C_1-C_4)$alkyl, phenyl which is unsubstituted or mono- or polysubstituted, preferably up to trisubstituted, by identical or different radicals selected from the group comprising halogen, $(C_1-C_4)$alkyl, $(C_1-C_4)$alkoxy, $(C_1-C_4)$haloalkyl, $(C_1-C_4)$haloalkoxy and nitro, or two of these radicals together are a $(C_2-C_6)$alkanediyl chain, and m=0 to 6, and a substituted alkoxy radical of the formula R"O—CHR'"(OR")$(C_1-C_6)$alkoxy in which the R" radicals independently of one another are $(C_1-C_4)$alkyl or together are $(C_1-C_6)$alkanediyl, and R'" is hydrogen or $(C_1-C_4)$alkyl, n' is an integer from 1 to 5, preferably 1 to 3, W' is a divalent heterocyclic radical of one of the formulae W1 to W4,

$R^{32}$ is hydrogen, $(C_1-C_8)$alkyl, $(C_1-C_8)$haloalkyl, $(C_3-C_{12})$cycloalkyl or optionally substituted phenyl and $R^{33}$ is hydrogen, $(C_1-C_8)$alkyl, $(C_1-C_8)$haloalkyl, $(C_1-C_4)$alkoxy$(C_1-C_4)$alkyl, $(C_1-C_6)$hydroxyalkyl, $(C_3-C_{12})$cycloalkyl or tri$(C_1-C_4)$alkylsilyl.

Particularly of interest as herbicidal agents are those in which, in formula A,

X is an oxygen atom,

Y is N or CH, preferably CH, $R^2$ and $R^3$ independently of one another are $(C_1-C_4)$alkyl, $(C_1-C_4)$alkoxy or $(C_1-C_4)$haloalkoxy, preferably methyl or methoxy, $R^4$ and $R^5$ independently of one another are hydrogen, halogen, cyano, $(C_1-C_4)$alkyl, $(C_1-C_4)$alkoxy, $(C_1-C_4)$haloalkyl or $(C_1-C_4)$haloalkoxy, the preferred meaning of $R^4$ being hydrogen, halogen, $(C_1-C_2)$alkyl, $(C_1-C_2)$alkoxy, $(C_1-C_2)$haloalkyl or $(C_1-C_2)$haloalkoxy and that of $R^5$ being hydrogen, or —$CR^{14}R^{15}R^{16}$ is isopropyl, t-butyl or cyclopentyl, or if a compound of the formula A contains said general radicals together, also those compounds of the formula A which contain a combination of the radicals mentioned as being preferred.

Other particularly interesting herbicidal agents are those in which, in formula B1, $R^{31}$ is hydrogen, $(C_1-C_8)$alkyl or $(C_3-C_7)$cycloalkyl, where the above carbon-containing radicals are unsubstituted or mono- or polysubstituted by halogen or mono- or disubstituted, preferably up to monosubstituted, by radicals selected from the group comprising hydroxyl, $(C_1-C_4)$alkoxy, $(C_1-C_4)$alkoxycarbonyl, $(C_2-C_6)$alkenyloxycarbonyl, $(C_2-C_6)$alkynyloxycarbonyl, 1-(hydroxyimino)$(C_1-C_4)$alkyl, 1-[$(C_1-C_4)$alkylimino]$(C_1-C_4)$alkyl, 1-[$(C_1-C_4)$alkoxyimino]$(C_1-C_4)$alkyl and radicals of the formulae —$SiR'_3$, —O—N=$CR'_2$, —N=$CR'_2$ and —O—$NR'_2$ in which the R' radicals in said formulae independently of one another are hydrogen or $(C_1-C_4)$alkyl, or two of these radicals together are a $(C_4-C_5)$alkanediyl chain, $R^{32}$ is hydrogen, $(C_1-C_8)$alkyl, $(C_1-C_6)$haloalkyl, $(C_3-C_7)$cycloalkyl or phenyl and $R^{33}$ is hydrogen, $(C_1-C_8)$alkyl, $(C_1-C_8)$haloalkyl, $(C_1-C_4$alkoxy$)(C_1-C_4)$alkyl, $(C_1-C_6)$hydroxyalkyl, $(C_3-C_7)$cycloalkyl or tri$(C_1-C_4)$alkylsilyl, and herbicidal agents in which X' is hydrogen, halogen, methyl, ethyl, methoxy, ethoxy, $(C_1$ or $C_2)$haloalkyl, preferably hydrogen, halogen or $(C_1$ or $C_2)$haloalkyl.

Preferred herbicidal agents are those in which, in formula B1,

X' is hydrogen, halogen, nitro or $(C_1-C_4)$haloalkyl, n' is 1, 2 or 3,

Z' is a radical of the formula $OR^{31}$, $R^{31}$ is hydrogen, $(C_1-C_8)$alkyl or $(C_3-C_7)$cycloalkyl, where the above carbon-containing radicals are unsubstituted or mono- or polysubstituted, preferably up to trisubstituted, by identical or different halogen radicals or up to disubstituted, preferably unsubstituted or monosubstituted, by identical or different radicals selected from the group comprising hydroxyl, $(C_1-C_4)$alkoxy, $(C_1-C_4)$alkoxycarbonyl, $(C_2-C_6)$alkenyloxycarbonyl, $(C_2-C_6)$alkynyloxycarbonyl, 1-(hydroxyimino)$(C_1-C_4)$alkyl, 1-[$(C_1-C_4)$alkylimino]$(C_1-C_4)$alkyl, 1-[$(C_1-C_4)$alkoxyimino]$(C_1-C_4)$alkyl and the radicals of the formulae —$SiR'_3$, —O—N=$R'_2$, —N=$CR'_2$ and —O—$NR'_2$, in which the radicals R' in said formulae independently of one another are hydrogen or $(C_1-C_4)$alkyl, or two of these radicals together are $(C_4$ or $C_5)$alkanediyl, $R^{32}$ is hydrogen, $(C_1-C_8)$alkyl, $(C_1-C_6)$haloalkyl, $(C_3-C_7)$cycloalkyl or phenyl and $R^{33}$ is hydrogen, $(C_1-C_8)$alkyl, $(C_1-C_8)$haloalkyl, $(C_1-C_4)$alkoxy$(C_1-C_4)$alkyl, $(C_1-C_6)$hydroxyalkyl, $(C_3-C_7)$cycloalkyl or tri$(C_1-C_4)$alkylsilyl.

Other preferred herbicidal agents are those in which, in formula B2,

X' is hydrogen, halogen or $(C_1-C_4)$haloalkyl, n is 1, 2 or 3, where $(X')_n$ is preferably 5-Cl, Z' is a radical of the formula $OR^{31}$, R* is $CH_2$ and $R^{31}$ is hydrogen, $(C_1-C_8)$alkyl, $(C_1-C_8)$haloalkyl or $(C_1-C_4)$alkoxy$(C_1-C_4)$alkyl, 1-(hydroxyimino)$(C_1-C_4)$alkyl, 1-[$(C_1-C_4)$alkylimino]$(C_1-C_4)$alkyl, 1-[$(C_1-C_4)$alkoxyimino]$(C_1-C_4)$alkyl, preferably $(C_1-C_8)$alkyl.

Particularly preferred herbicidal agents are those in which, in formula B1,

W' is W1,

X' is hydrogen, halogen or $(C_1-C_2)$haloalkyl, n' is 1, 2 or 3, where $(X')_n$ is preferably 2,4-$Cl_2$, Z' is a radical of the formula $OR^{31}$, $R^{31}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy$(C_1-C_4)$alkyl, tri$(C_1-C_2)$alkylsilyl, preferably $(C_1-C_4)$alkyl, $R^{32}$ is hydrogen, $(C_1-C_8)$alkyl, $(C_1-C_4)$haloalkyl or $(C_3-C_7)$cycloalkyl, preferably hydrogen or $(C_1-C_4)$alkyl, and $R^{33}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4)$alkoxy$(C_1-C_4)$alkyl or tri$(C_1-C_2)$alkylsilyl, preferably hydrogen or $(C_1-C_4)$alkyl.

Other particularly preferred herbicidal agents are those in which, in formula B1, W' is W2, X' is hydrogen, halogen or $(C_1-C_2)$haloalkyl, n' is 1, 2 or 3, where $(X')_n$ is preferably 2,4-$Cl_2$, Z' is a radical of the formula $OR^{31}$, $R^{31}$ is hydrogen, $(C_1-C_8)$alkyl, $(C_1-C_4)$haloalkyl, $(C_1-C_4)$hydroxyalkyl, $(C_3-C_7)$cycloalkyl, $(C_1-C_4$alkoxy$)C_1-C_4$alkyl, tri$(C_1-C_2)$alkylsilyl, preferably $(C_1-C_4)$alkyl, and $R^{32}$ is hydrogen, $(C_1-C_8)$alkyl, $(C_1-C_4)$haloalkyl, $(C_3-C_7)$cycloalkyl or phenyl, preferably hydrogen or $(C_1-C_4)$alkyl.

Other particularly preferred herbicidal agents are those in which, in formula B1, W' is W3, X' is hydrogen, halogen or $(C_1-C_2)$haloalkyl n' is 1, 2 or 3, where $(X')_n$ is preferably 2,4-$Cl_2$, Z' is a radical of the formula $OR^{31}$, $R^{31}$ is hydrogen, $(C_1-C_8)$alkyl, $(C_1-C_4)$haloalkyl, $(C_1-C_4$hydroxyalkyl, $(C_3-C_7)$cycloalkyl, $(C_1-C_4)$-alkoxy$(C_1-C_4)$alkyl, tri$(C_1-C_2)$alkylsilyl, preferably $(C_1-C_4)$alkyl, and $R^{32}$ is $(C_1-C_8)$alkyl or $(C_1-C_4)$haloalkyl, preferably $C_1$-haloalkyl.

Other particularly preferred herbicidal agents are those in which, in formula B1, W' is W4, X' is hydrogen, halogen, nitro, $(C_1-C_4)$alkyl or $(C_1-C_2)$haloalkyl, preferably $CF_3$, or $(C_1-C_4)$alkoxy, n' is 1, 2 or 3, Z' is a radical of the formula $OR^{31}$, $R^{31}$ is hydrogen, $(C_1-C_4)$alkyl or $(C_1-C_4)$alkoxycarbonyl$(C_1-C_4)$alkyl, preferably $(C_1-C_4)$alkoxy—CO—$CH_2$—, $(C_1-C_4)$alkoxy—CO—$C(CH_3)H$—, HO—CO—$CH_2$— or HO—CO—$C(CH_3)H$—.

Unless specifically defined otherwise, the following definitions apply to the radicals in formulae A, B1 and B2: alkyl, alkenyl and alkynyl are straight-chain or branched and have up to 8, preferably up to 4, carbon atoms; this applies analogously to the aliphatic moiety of substituted alkyl, alkenyl and alkynyl radicals or radicals derived therefrom, such as haloalkyl, hydroxyalkyl, alkoxycarbonyl, alkoxy, alkanoyl, haloalkoxy and the like.

Alkyl is, for example, methyl, ethyl, n- and isopropyl, n-, iso-, tert.- and 2-butyl, pentyl radicals and hexyl radicals such as n-hexyl, isohexyl and 1,3-dimethylbutyl, and heptyl radicals such as n-heptyl, 1-methylhexyl and 1,4-dimethylpentyl. Alkenyl is, for example, allyl, 1-methylprop-2-en-1-yl, but-2-en-1-yl, but-3-en-1-yl, 1-methylbut-3-en-1-yl and 1-methylbut-2-en-1-yl. Alkynyl is, for example, propargyl, but-2-in-1-yl, but-3-in-1-yl and 1-methyl-but-3-ine.

Cycloalkyl preferably has 3 to 8 carbon atoms and is, for example, cyclobutyl, cyclopentyl, cyclohexyl or cycloheptyl. If appropriate, cycloalkyl can have up to two $(C_1-C_4)$alkyl radicals as substituents.

Halogen is fluorine, chlorine, bromine or iodine, preferably fluorine, chlorine or bromine, in particular fluorine or chlorine. Haloalkyl, haloalkenyl and haloalkynyl are alkyl, alkenyl and alkynyl, respectively, which are mono-, di- or polysubstituted by halogen, such as $CF_3$, $CHF_2$, $CH_2F$, $CF_3CF_2$, $CH_2FCHCl$, $CCl_3$, $CHCl_2$ or $CH_2CH_2Cl$. Examples of haloalkoxy are $OCF_3$, $OCHF_2$, $OCH_2F$, $CF_3CF_2O$ and $CF_3CH_2O$.

Aryl has 6 to 12 carbon atoms and is, for example, phenyl, naphthyl or biphenylyl, but preferably phenyl. This applies analogously to radicals derived therefrom, such as aryloxy, aroyl or aryloxyalkyl. Optionally substituted phenyl is, for example, phenyl which is unsubstituted or has one, two or three identical or different substituents selected from the group comprising halogen, $(C_1-C_4)$alkyl, $(C_1-C_4)$alkoxy, $(C_1-C_4)$haloalkyl, $(C_1-C_4)$haloalkoxy and nitro, such as o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl or o-, m- and p-methoxyphenyl.

The compounds of the formulae B1 are known from EP-A-333,131 (ZA-89/1960), EP-A-269,806 (U.S. Pat. No. 4,891,057), EP-A-346,620 (AU-A-89/34951) and the international patent applications PCT/EP 90/01966 (WO-91/08202) and PCT/EP 90/02020 (WO-91/07874) and from the literature cited therein, or they can be prepared by, or analogously to, the processes described therein. The compounds of the formula B2 are known from EP-A-94,349 (U.S. Pat. No. 4,902,340) and EP-A-191,736 (U.S. Pat. No. 4,881,966) and from the literature cited therein or can be prepared by, or analogously to, the processes described therein. Some compounds are also described in German Patent Application P 40 41 121.4.

Suitable herbicidal active substances according to the invention are those pyrimidine or triazine derivatives of the formula A which cannot, or cannot optimally, be used on their own in cereal crops and/or corn because they damage the crop plants unduly.

The compounds of the formula A are known from EP-A-372,329, EP-A-363,040, EP-330,990, JP 88-118,929, EP-A-335,409, EP-A-249,707 and EP-A-347,811 and from the literature cited therein or can be prepared by analogous processes.

The following groups of compounds have proved themselves suitable as safeners for the abovementioned herbicidal active substances:

a) Compounds of the dichlorophenylpyrazoline-3-carboxylic acid type (i.e. of the formula B1 in which W'=W1 and $(X')_n$=2,4-$Cl_2$), preferably compounds such as ethyl 1-(2,4-dichlorophenyl)-5-(ethoxycarbonyl)-5-methyl-2-pyrazoline-3-carboxylate (B1-1) and related compounds as they are described in the international application PCT/EP 90/02020, b) dichlorophenylpyrazolecarboxylic acid derivatives (i.e. of the formula B1 in which W'=W2 and $(X')_n$=2,4-$Cl_2$), preferably compounds such as ethyl 1-(2,4-dichlorophenyl)-5-methylpyrazole-3-carboxylate (B1-2), ethyl 1-(2,4-dichlorophenyl)-5-isopropylpyrazole-3-carboxylate (B1-3), ethyl 1-(2,4-dichlorophenyl)-5-(1,1-dimethylethyl)pyrazole-3-carboxylate (B1-4), ethyl 1-(2,4-dichlorophenyl)-5-phenylpyrazole-3-carboxylate (B1-5) and related compounds as they are described in EP-A-333,131 and EP-A-269,806.

c) Compounds of the triazolecarboxylic acid type (i.e. of the formula B1 in which W'=W3 and $(X')_n$=2,4-$Cl_2$), preferably compounds such as ethyl 1-(2,4-dichlorophenyl)-5-trichloromethyl-(1H)-1,2,4-triazole-3-carboxylate (B1-6, fenchlorazol) and related compounds (see EP-A-174,562 and EP-A-346,620);

d) Compounds of the dichlorobenzyl-2-isoxazoline-3-carboxylic acid type (i.e. of the formula B1 in which W'=W4 and $(X')_n$=2,4-$Cl_2$), preferably compounds such as ethyl 5-(2,4-dichlorobenzyl)-2-isoxazoline-3-carboxylate (B1-7) and related compounds as they are described in the international application PCT/EP 90/01966.

e) Compounds of the 8-quinolinoxyacetic acid type, for example those of the formula B2 in which $(X')_n$=5-Cl, hydrogen, $Z'=OR^{31}$, $R^*=CH_2$), preferably compounds such as 1-methylhex-1-yl (5-chloro-8-quinolinoxy)acetate (B2-1),
1,3-dimethylbut-1-yl (5-chloro-8-quinolinoxy)acetate (B2-2),
4-allyloxybutyl (5-chloro-8-quinolinoxy)acetate (B2-3),
1-allyloxyprop-2-yl (5-chloro-8-quinolinoxy)acetate (B2-4),
ethyl (quinolin-8-oxy)acetate (B2-5),
methyl (5-chloro-8-quinolinoxy)acetate (B2-6),
allyl (5-chloro-8-quinolinoxy)acetate (B2-7),
2-(2-propylidene-iminoxy)-1-ethyl (5-chloro-8-quinolinoxy)acetate (B2-8),
2-oxoprop-1-yl (5-chloro-8-quinolinoxy)acetate (B2-9) and related compounds as they are described in EP-A-86,750, EP-A-94,349 and EP-A-191,736 or proposed in German Patent Application P 40 41 121.4.

The safeners (antidotes) of the above groups a) to e) reduce, or prevent, phytotoxic effects which can occur when the herbicidal active substances of the formula A are employed in crops of useful plants, without adversely affecting the activity of these herbicidal active substances against weeds. This allows the field of application of conventional crop protection agents to be widened considerably and to be extended, for example, to crops such as wheat, barley, maize and other Gramineae crops in which the use of the herbicides was hitherto not possible, or possible to a limited extent only, i.e. at low dosage rates and with a narrow spectrum of action.

The herbicidal active substances and said safeners can be applied together (as a finished formulation or by the tank mix method) or in any desired sequence one after the other. The ratio by weight of safener:herbicidal active substance can vary within wide limits and is preferably in the range of from 1:10 to 10:1, in particular of from 1:10 to 5:1. The amounts of herbicidal active substance and safener which are optimal in each case depend on the nature of the herbicidal active substance used or on the safener used as well as on the nature of the plant stand to be treated, and the amounts can be determined in every single case by suitable preliminary experiments.

The safeners are mainly used in corn and cereal crops (wheat, rye, barley, oats), rice, sorghum, but also cotton and soybeans, preferably cereals and corn.

Depending on their properties, the safeners of the formulae B1 and B2 can be used for pre-treating the seed of the crop plant (seed dressing), or they can be incorporated in the seed furrows prior to sowing, or used together with the herbicide prior to, or after, plant emergence. Pre-emergence treatment includes both the treatment of the area under cultivation prior to sowing and treatment of the areas under cultivation where seed has been sown but growth of the crop plants has not yet taken place. Application together with the herbicide is preferred. Tank mixes or ready-to-use formulations can be employed for this purpose.

Depending on the indication and the herbicidal active substance used, the required application rates of the safeners can vary within wide limits, and they are generally in the range from 0.001 to 5 kg, preferably 0.005 to 0.5 kg, of active substance per hectare.

The present invention therefore also relates to a method of protecting crop plants against phytotoxic secondary effects of herbicides, which comprises applying an effective amount of a compound of the formula B1 and/or B2 before, after, or together with the herbicidal active substance, of the formula A, to the plants, seeds of plants or the area under cultivation.

The compounds of the formulae B1 and B2 and their combinations with one or more of the herbicidal active substances mentioned can be formulated in a variety of ways, as predetermined by the biological and/or physio-chemical parameters. The following possibilities are therefore suitable for formulation: wettable powders (WP), emulsifiable concentrates (EC), watersoluble powders (SP), water-soluble concentrates (SL), concentrated emulsions (BW) such as oil-in-water and water-in-oil emulsions, sprayable solutions or emulsions, capsule suspensions (CS), dispersions on an oil or water base (SC), suspoemulsions, suspension concentrates, dusting agents (DP), solutions which are miscible with oil (ÖL), seed-dressing agents, granules (GR) in the form of microgranules, spray granules, coated granules and adsorption granules, granules for soil application and for broadcasting, water-soluble granules (SG), water-dispersible granules (WG), ULV formulations, microcapsules and waxes.

These individual formulation types are known in principle and are described, for example, in: Winnacker-Küchler, "Chemische Technologie [Chemical Technology]", Volume 7, C. Hauser Verlag Munich, 4th Ed., 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell N.J.; H. v. Olphen, "Intruduction to Clay Colloid Chemistry", 2nd Ed., J. Wiley & Sons, N.Y.; Marsden, "Solvents Guide", 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986.

Combinations with other pesticidally active substances, fertilizers and/or growth regulators may also be prepared on the basis of these formulations, for example in the form of a ready-to-use formulation or as a tank mix.

Wettable powders are preparations which are uniformly dispersible in water and which, besides the active substance, also contain ionic and/or nonionic surfactants (wetting agents, dispersants) for example polyethoxylated alkylphenols, polyethoxylated fatty alcohols and fatty amines, fatty alcohol polyglycol ether sulfates, alkanesulfonates or alkylarylsulfonates, sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance.

Emulsifiable concentrates are prepared by dissolving the active substance in an organic solvent, for example butanol, cyclohexanone, dimethylformamide, xylene and also higher-boiling aromatic compounds or hydrocarbons, with the addition of one or more ionic and/or nonionic surfactants (emulsifiers). Examples of emulsifiers which can be used are: calcium alkylarylsulfonates, such as calcium dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products (for example block copolymers), alkyl polyethers, sorbitan fatty acid esters, polyoxyethylene sorbitan fatty acid esters or other polyoxyethylene sorbitan esters. Dusting agents can be obtained by grinding the active substance with finely divided solid substances, for example talc or natural clays, such as kaolin, bentonite and pyrophillite, or diatomaceous earth.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Water-dispersible granules are generally prepared by the customary processes such as spray-drying, fluidized bed granulation, disk granulation, mixing by means of high-speed mixers, and extrusion without solid inert material. Suitable active substances can also be granulated in the manner which is conventional for the production of fertilizer granules, if desired in a mixture with fertilizers.

The agrochemical preparations generally contain 0.1 to 99% by weight, in particular 0.1 to 95% by weight, of active substances of the formula B1 and/or B2 or of the herbicide/ antidote active substance mixture A and B1 and/or B2, and 1 to 99.9% by weight, in particular 5 to 99.8% by weight, of a solid or liquid additive, and 0 to 25% by weight, in particular 0.1 to 25% by weight, of a surfactant.

The concentration of active substance in wettable powders is, for example, about 10 to 90% by weight; the remainder to 100% by weight is composed of conventional formulation components. In the case of emulsifiable concentrates, the concentration of active substance can be about 1 to 80% by weight. Formulations in the form of dusts usually contain 1 to 20% by weight, sprayable solutions about 0.2 to 20% by weight, of active substances. In the case of granules, such as water-dispersible granules the active substance content depends partly on whether the active compound is liquid or solid. As a rule, the content in the water-dispersible granules is between 10 and 90% by weight.

In addition, the active substance formulations mentioned contain, if appropriate, the adhesives, wetting agents, dispersing agents, emulsifiers, penetrants, solvents, fillers or carriers which are conventional in each case.

For use, the formulations, present in commercially available form, are diluted, if appropriate, in a customary manner, for example using water in the case of wettable powders, emulsifiable concentrates, dispersions and water-dispersible granules. Preparations in the form of dusts, granules and also sprayable solutions are usually not further diluted with other inert substances before use. Particularly good activity of the agents according to the invention can be achieved by adding more wetting agents in concentrations of from 0.1 to 0.5% by weight in the tank mix method, for example non-ionic wetting agents or wetting agents of the type of fatty alcohol polyol ether sulfates, in addition to the surfactants contained in the formulations (see, for example, German Patent Application P 40 29 304.1). The application rate required for the safeners varies with the external conditions, such as, inter alia, temperature, humidity, and the nature of the herbicide used.

The examples which follow serve to illustrate the invention:

A. FORMULATION EXAMPLES a) A dusting agent is obtained by mixing 10 parts by weight of a compound of the formula B1 and/or B2 or of an active substance mixture of a herbicidal active substance of the formula A and a safener of the formula B1 and/or B2 and 90 parts by weight of talc or inert substance and comminuting the mixture in a hammer mill.

b) A wettable powder which is readily dispersible in water is obtained by mixing 25 parts by weight of a compound of the formula B1 and/or B2 or of an active substance mixture of a herbicidal active substance of the formula A and a safener of the formula B1 and/or B2, 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk mill.

c) A dispersion concentrate which is readily dispersible in water is obtained by mixing 20 parts by weight of a compound of the formula B1 and/or B2 or of an active substance mixture of a herbicidal active substance of the formula A and a safener of the formula B1 and/or B2, 6 parts by weight of alkylphenol polyglycol ether (®Triton X 207), parts by weight of isotridecanol polyglycol ether (8 EO) and 71 parts by weight of paraffinic mineral oil (boiling range, for example, about 255° to above 277°.C.), and grinding the mixture in a ball mill to a fineness of below 5 microns.

d) An emulsifiable concentrate is obtained from 15 parts by weight of a compound of the formula B1 and/or B2 or of an active substance mixture of a herbicidal active substance of the formula A and a safener of the formula B1 and/or B2, 75 parts by weight of cyclohexanone as the solvent and 10 parts by weight of ethoxylated nonylphenol as the emulsifier.

e) Water-dispersible granules are obtained by mixing

| | |
|---|---|
| 75 parts by weight | of a compound of the formula B1 and/or B2 or of an active substance mixture of a herbicidal active substance of the formula A and a safener of the formula B1 and/or B2, |
| 10 parts by weight | of calcium ligninsulfonate, |
| 5 parts by weight | of sodium lauryl sulfate, |
| 3 parts by weight | of polyvinyl alcohol and |
| 7 parts by weight | of kaolin, | grinding the mixture on a pinned disk mill and granulating the powder in a fluidized bed by spraying on water as the granulation liquid.

f) Water-dispersible granules are also obtained by homogenizing and precomminuting

| | |
|---|---|
| 25 parts by weight | of a compound of the formula B1 and/or B2 or of an active substance mixture of a herbicidal active substance of the formula A and a safener of the formula B1 and/or B2, |
| 5 parts by weight | of sodium 2,2'-dinaphthylmethane-6,6'-disulfonate, |
| 2 parts by weight | of sodium oleoylmethyltaurinate, |
| 1 part by weight | of polyvinyl alcohol, |
| 17 parts by weight | of calcium carbonate and |
| 50 parts by weight | of water | on a colloid mill, subsequently grinding the mixture on a bead mill, and atomizing and drying the resulting suspension in a spray tower by means of a single-substance nozzle.

B. BIOLOGICAL EXAMPLES

The crop plants and the broad-leaved and grass weeds were grown in plastic pots in the greenhouse until they had reached the 4-leaf stage and were then treated according to the invention with compounds of the formulae A and B1 and/or B2, by the post-emergence method. The compounds of the formulae A and B1 and/or B2 were applied in the form of aqueous suspensions or emulsions at a water application rate of 300 l/ha (converted). 4 weeks after the treatment, the plants were scored visually for any type of damage by the herbicides applied, with particular emphasis on the prolonged growth inhibition. The assessment was by percentages compared with untreated controls.

The results in the tables which follow illustrate that the compounds of the formula B1 or B2 which were employed according to the invention are capable of effectively reducing severe herbicide damage on crop plants caused by compounds of the formula A. Even when the herbicides are vastly overdosed, severe damage which occurs in the crop plants is markedly reduced, and lesser damage is compensated for completely.

Mixtures of herbicidal active substances of the formula A and compounds of the formula B1 and/or B2 are therefore outstandingly suitable for the selective weed control in crops such as cereals and maize.

Example 1: Herbicidal action and safener action

| | Dosage g A.I./ha | % Damage on crop plants and weeds | | |
|---|---|---|---|---|
| | | Corn | AMRE | ECCG |
| H1 | 400 | 55 | — | — |
| | 200 | 40 | — | — |
| | 100 | 20 | 100 | 100 |
| | 50 | 1 | 100 | 100 |
| H1 + B2-2 | 400 + 200 | 10 | — | — |
| | 200 + 100 | 0 | — | — |

| Example 1: Herbicidal action and safener action | | | | |
|---|---|---|---|---|
| | Dosage g A.I./ha | % Damage on crop plants and weeds | | |
| | | Corn | AMRE | ECCG |
| | 100 + 50 | 0 | 100 | 100 |
| | 50 + 25 | 0 | 100 | 100 |
| H1 + B2-3 | 400 + 200 | 0 | — | — |
| | 200 + 100 | 0 | — | — |
| | 100 + 50 | 0 | 100 | 100 |
| | 50 + 25 | 0 | 100 | 100 |
| H1 + B1-1 | 400 + 200 | 25 | — | — |
| | 200 + 100 | 5 | — | — |
| | 100 + 50 | 0 | 100 | 100 |
| | 50 + 25 | 0 | 100 | 100 |
| H1 + B2-4 | 400 + 200 | 5 | — | — |
| | 200 + 100 | 0 | — | — |
| | 100 + 50 | 0 | 100 | 100 |
| | 50 + 25 | 0 | 100 | 100 |

Abbreviations in the table in Example 1:

H1 =

Chemical name: 2-(2-benzyloxycarbonyl-pyrid-3-yloxy)-4,6-dimethoxypyrimidine
B1-1 = ethyl 1-(2,4-dichlorophenyl)-5-(ethoxy-carbonyl)-5-methyl-2-pyrazolin-3-carboxylate
B2-2 = 1,3-dimethylbut-1-yl (5-chloro-8-quinolinoxy)acetate,
B2-3 = 4-allyloxybutyl (5-chloro-8-quinolinoxy)-acetate,
B2-4 = 1-allyloxyprop-2-yl (5-chloro-8-quinolinoxy)acetate,
AMRE = *Amaranthus retroflexus*
ECCG = *Echinochloa crus galli*
A.I. = active ingredient (based on pure active substance)

| Example 2: Reduction of phytotoxicity by various antidotes | | |
|---|---|---|
| | Dosage in g of A.I./ha | % damage in corn |
| H1 | 400 | 55 |
| | 200 | 40 |
| | 100 | 20 |
| H1 + B2-5 | 400 + 200 | 15 |
| | 200 + 100 | 0 |
| | 100 + 50 | 0 |
| H1 + B2-6 | 400 + 200 | 10 |
| | 200 + 100 | 0 |
| | 100 + 50 | 0 |
| H1 + B2-1 | 400 + 200 | 10 |
| | 200 + 100 | 0 |
| | 100 + 50 | 0 |
| H1 + B1-3 | 400 + 200 | 5 |
| | 200 + 100 | 0 |
| | 100 + 50 | 0 |
| H1 + B1-7 | 400 + 200 | 15 |
| | 200 + 100 | 0 |
| | 100 + 50 | 0 |
| H1 + B2-7 | 400 + 200 | 10 |
| | 200 + 100 | 5 |
| | 100 + 50 | 0 |
| H1 + B2-8 | 400 + 200 | 10 |
| | 200 + 100 | 0 |
| | 100 + 50 | 0 |

| Example 2: Reduction of phytotoxicity by various antidotes | | |
|---|---|---|
| | Dosage in g of A.I./ha | % damage in maize |
| H1 + B2-9 | 400 + 200 | 15 |
| | 200 + 100 | 5 |
| | 100 + 50 | 0 |
| H2 | 200 | 70 |
| | 50 | 50 |
| | 25 | 35 |
| | 12 | 20 |
| H3 | 50 | 70 |
| | 25 | 40 |
| | 12 | 20 |
| H4 | 100 | 80 |
| | 50 | 45 |
| | 25 | 20 |
| | 12 | 5 |
| H5 | 50 | 40 |
| | 25 | 30 |
| | 12 | 20 |
| H2 + B2-6 | 100 + 100 | 25 |
| | 50 + 50 | 5 |
| | 25 + 25 | 0 |
| | 12 + 12 | 0 |
| H3 + B2-8 | 50 + 50 | 20 |
| | 25 + 25 | 0 |
| | 12 + 12 | 0 |
| H4 + B2-4 | 100 + 100 | 35 |
| | 50 + 50 | 5 |
| | 25 + 25 | 0 |
| | 12 + 12 | 0 |
| H5 + B2-2 | 50 + 50 | 5 |
| | 25 + 25 | 0 |
| | 12 + 12 | 0 |

Abbreviations in the table of Example 2:
H1 = see table for Biological Example 1
H2 = 2-(2-methoxycarbonyl-pyrid-3-yloxy)-4,6-dimethoxypyrimidine,
H3 = 2-(2-carboxyphenoxy)-4,6-dimethoxypyrimidine,
H4 = 2-(2-methoxycarbonylphenoxy)-4,6-dimethoxypyrimidine,
H5 = 2-(1-carboxy-2-methylpropoxy)-4,6-dimethoxypyrimidine
B1-3 = ethyl 1-(2,4-dichlorophenyl)-5-isopropylpyrazole-3-carboxylate,
B1-7 = ethyl 5-(2,4-dichlorobenzyl)-2-isoxazoline-3-carboxylate,
B2-1 = 1-methylhex-1-yl (5-chloro-8-quinolinoxy)acetate,
B2-2 = see table for Biological Example 1
B2-4 = see table for Biological Example 1
B2-5 = ethyl (8-quinolinoxy)acetate
B2-6 = methyl (5-chloro-8-quinolinoxy)acetate
B2-7 = allyl (5-chloro-8-quinolinoxy)acetate
B2-8 = 2-2-(propylidene-iminoxy)-1-ethyl (5-chloro-8-quinolinoxy)acetate
B2-9 = 2-oxoprop-1-yl (5-chloro-8-quinolinoxy)acetate

We claim:

1. A herbicidal agent which contains

A) at least one herbicidal active substance from the group of the substituted pyrimidines and triazines of the formula A $$R^1-X-\underset{N}{\overset{N}{\bigwedge}}\overset{R^3}{\underset{R^2}{\bigvee}}Y \quad (A)$$

in which
X is O, S or NR$^4$,
Y is N or CH,
R$^2$ and R$^3$ independently of one another are hydrogen, (C$_1$–C$_4$)alkyl, (C$_1$–C$_4$)haloalkyl, (C$_1$–C$_4$)alkoxy, (C$_1$–C$_4$)haloalkoxy, (C$_1$–C$_4$)alkylmercapto, (C$_1$–C$_4$)alkylamino or di(C$_1$–C$_4$)alkylamino, $R^1$ is a substituted aryl or heteroaryl radical of the formula

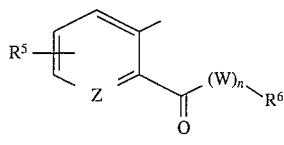

or

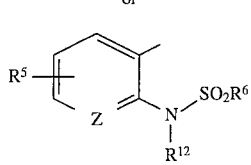

n is 0 or 1,
W is —O—, —$NR^4$—, —S—, —$ON(R^{11})$— or —O—N=$C(R^{11})$—,
Z is N, N→O or $CR^4$,
$R^4$ and $R^5$ independently of one another are hydrogen, halogen, cyano, $(C_1-C_4)$alkyl, $(C_2-C_4)$alkenyl, $(C_2-C_4)$alkynyl, $(C_1-C_4)$alkoxy, $(C_2-C_4)$alkenyloxy, $(C_2-C_4)$alkynyloxy, benzyloxy, 4,6-di[$(C_1-C_4)$alkoxy]pyrimidin-2-yloxy, $(C_1-C_4)$alkylthio, $(C_2-C_4)$alkenylthio, $(C_2-C_4)$alkynylthio, benzylthio, $(C_1-C_4)$alkylamino, di[$(C_1-C_4$-alkyl]-amino, $(C_1-C_4)$haloalkyl or $(C_1-C_4)$haloalkoxy,
$R^6$ is hydrogen, $(C_1-C_4)$alkyl, $(C_2-C_4)$alkenyl, $(C_2-C_4)$alkynyl, alkali metal or 1 equivalent alkaline earth metal, alkylammonium, aryl, $CF_3$ or $(CHR^{13})_{m'}CHR^7R^8$ where m' is 0 or 1,
$R^7$ and $R^{13}$ independently of one another are hydrogen, $(C_1-C_4)$alkyl or $(C_1-C_4)$alkoxy,
$R^8$ is $(C_1-C_4)$alkoxycarbonyl, cyano, halogen, acetyl, pivaloyl, benzoyl, $(C_1-C_4)$alkoxy, aryloxy, haloacetoxy, methanesulfonyloxy, hydroxyl, $(C_1-C_4)$alkylmercapto, $(C_1-C_4)$alkylsulfonyl, arylmercapto, di-$(C_1-C_4)$alkylamino, pyridyl, aryl or $CONR^9R^{10}$,
$R^9$ and $R^{10}$ independently of one another are hydrogen, $(C_1-C_4)$alkyl, $(C_2-C_4)$alkenyl, aryl or benzyl,
$R^{11}$ is hydrogen or $(C_1-C_4)$alkyl or
$R^6$ and $R^{11}$ together are methylene, ethanediyl or propanediyl,
$R^{12}$ is hydrogen, alkyl or alkoxy and
aryl is phenyl or naphthyl, each of which is unsubstituted or mono- or disubstituted by radicals selected from the group comprising halogen, $(C_1-C_4)$alkyl, $(C_1-C_4)$alkoxy, phenoxy, nitro and $(C_1-C_4)$alkoxycarbonyl, or
$R^1$ is a radical of the formula

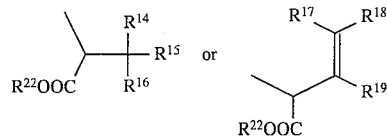

$R^{14}$ is hydrogen, halogen, halo $(C_1-C_4)$alkyl, $(C_1-C_4)$alkyl, cycloalkyl, $(C_1-C_4)$alkylmercapto$(C_1-C_4)$alkyl, hydroxy$(C_1-C_4)$alkyl, hydroxyl, cyano, aryloxy$(C_1-C_4)$alkyl, thienyl, aryl, dihydronaphthyl or

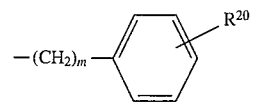

where aryl is as defined above,
$R^{20}$ is hydrogen, halogen, nitro, $(C_1-C_4)$alkyl, $(C_1-C_4)$alkoxy or $S(O)_pR^{21}$,
$R^{21}$ is alkyl,
p is 0, 1 or 2,
m is 0, 1 or 2,
$R^{15}$ and $R^{16}$ independently of one another are hydrogen or alkyl, or together with the carbon atom form a 3-, 4-, 5- or 6-membered cycloalkane ring in which a methylene group can be replaced by oxygen and which can be substituted by one or two alkyl groups,
$R^{17}$ and $R^{18}$ independently of one another are hydrogen or $(C_1-C_4)$alkyl,
$R^{19}$ is $(C_1-C_4)$alkyl or phenyl, or
$R^{18}$ and $R^{19}$ are —$(CH_2)_l$— where l is 3 or 4 and which can be substituted by one or two alkyl groups,
$R^{22}$ is hydrogen, $(C_1-C_4)$alkyl, $(C_1-C_4)$alkenyl, $(C_1-C_4)$alkynyl, phenyl, $(C_1-C_4)$alkylideneamino, $(C_1-C_4)$alkoxycarbonyl$(C_1-C_4)$alkyl, $(C_1-C_4)$alkoxy$(C_1-C_4)$alkyl, halo$(C_1-C_4)$alkyl, cycloalkyl, nitro-substituted phenylmercapto$(C_1-C_4)$alkyl, halogen or benzyl which can be substituted by $(C_1-C_4)$alkyl or $(C_1-C_4)$alkoxy,
or a salt thereof, and
B) at least one compound from the group of the safener compounds of the formulae B1 and B2

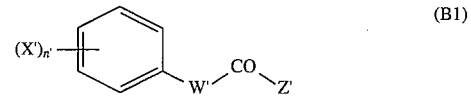 (B1)

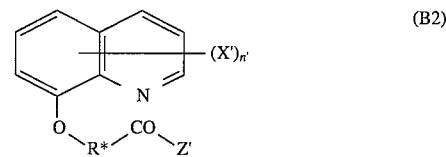 (B2)

in which
X' is hydrogen, halogen, $(C_1-C_4)$alkyl, $(C_1-C_4)$alkoxy, nitro or $(C_1-C_4)$haloalkyl,
Z' is $OR^{31}$, $SR^{31}$ or $NR^{31}R$, or forms a saturated or unsaturated 3- to 7-membered heterocycle which has at least one nitrogen atom and up to 3 hetero atoms, which is linked to the carbonyl group via the nitrogen atom and which is unsubstituted or substituted by radicals selected from the group comprising $(C_1-C_4)$alkyl, $(C_1-C_4)$alkoxy or optionally substituted phenyl,
R is hydrogen, $(C_1-C_6)$alkyl, $(C_1-C_6)$alkoxy or optionally substituted phenyl,
R* is a $(C_1$ or $C_2)$alkanediyl chain which can additionally be substituted by one or two $(C_1-C_4)$alkyl radicals,
$R^{31}$ is hydrogen, $(C_1-C_{18})$alkyl, $(C_3-C_{12})$cycloalkyl, $(C_2-C_8)$alkenyl or $(C_2-C_8)$alkynyl, where the above carbon-containing radicals are unsubstituted or mono- or polysubstituted by identical or different radicals selected from the group comprising halogen, hydroxyl, $(C_1-C_8)$alkoxy, $(C_1-C_8)$alkylmercapto, $(C_2-C_8)$alkenylmercapto, $(C_2-C_8)$alkynylmercapto, ($C_2$-$C_8$)alkenyloxy, ($C_2$-$C_8$)alkynyloxy, ($C_3$-$C_7$)cycloalkyl, ($C_3$-$C_7$)cycloalkoxy, cyano, mono- and di($C_1$-$C_4$alkyl)amino, ($C_1$-$C_8$)alkoxycarbonyl, ($C_2$-$C_8$)alkenyloxycarbonyl, ($C_1$-$C_8$)alkylmercaptocarbonyl, ($C_2$-$C_8$)alkynyloxycarbonyl, ($C_1$-$C_8$)alkylcarbonyl, ($C_2$-$C_8$)alkenylcarbonyl, ($C_2$-$C_8$)alkynylcarbonyl, 1-(hydroxyimino)($C_1$-$C_6$)alkyl, 1-[($C_1$-$C_4$)alkylimino]($C_1$-$C_4$)alkyl, 1-[($C_1$-$C_4$)alkoxyimino]($C_1$-$C_6$)alkyl, ($C_1$-$C_8$)alkylcarbonylamino, ($C_2$-$C_8$)alkenylcarbonylamino, ($C_2$-$C_8$)alkynylcarbonylamino, aminocarbonyl, ($C_1$-$C_8$)alkylaminocarbonyl, di-($C_1$-$C_6$)alkylaminocarbonyl, ($C_2$-$C_6$)alkenylaminocarbonyl, ($C_2$-$C_6$)alkynylaminocarbonyl, ($C_1$-$C_8$)alkoxycarbonylamino, ($C_1$-$C_8$)alkylaminocarbonylamino, ($C_1$-$C_6$)alkylcarbonyloxy which is unsubstituted or substituted by halogen, nitro, ($C_1$-$C_4$)alkoxy or optionally substituted phenyl, or ($C_2$-$C_6$)alkenylcarbonyloxy, ($C_2$-$C_6$)alkynylcarbonyloxy, ($C_1$-$C_8$)alkylsulfonyl, phenyl, phenyl($C_1$-$C_6$)alkoxy, phenyl($C_1$-$C_6$)alkoxycarbonyl, phenoxy, phenoxy($C_1$-$C_6$)alkoxy, phenoxy($C_1$-$C_6$)alkoxycarbonyl, phenylcarbonyloxy, phenylcarbonylamino, phenyl($C_1$-$C_6$)alkylcarbonylamino, the last 9 radicals mentioned being unsubstituted in the phenyl ring or mono- or polysubstituted by radicals selected from the group comprising halogen, ($C_1$-$C_4$)alkyl, ($C_1$-$C_4$)alkoxy, ($C_1$-$C_4$)haloalkyl, ($C_1$-$C_4$)haloalkoxy and nitro, and radicals of the formulae —$SiR'_3$, —O—$SiR'_3$, $R'_3Si$($C_1$-$C_8$)alkoxy, —CO—O—$NR'_2$, —O—N=$CR'_2$, —N=$CR'_2$, —O—$NR'_2$—CH($OR'$)$_2$ and —O—($CH_2$)$_m$—CH($OR'$)$_2$, where the R' radicals in said formulae independently of one another are hydrogen, ($C_1$-$C_4$)alkyl, phenyl which is unsubstituted or mono- or polysubstituted by radicals selected from the group comprising halogen, ($C_1$-$C_4$)alkyl, ($C_1$-$C_4$)alkoxy, ($C_1$-$C_4$)haloalkyl, ($C_1$-$C_4$)haloalkoxy and nitro, or two of these radicals together are a ($C_2$-$C_6$)alkanediyl chain, and m=0 to 6, and a substituted alkoxy radical of the formula R"O—CHR'"(OR")($C_1$-$C_6$)alkoxy in which the R" radicals independently of one another are ($C_1$-$C_4$)alkyl or together are ($C_1$-$C_4$)alkanediyl, and R'" is hydrogen or ($C_1$-$C_4$)alkyl, n' is an integer from 1 to 5, W' is a divalent heterocyclic radical of one of the formulae W1 to W4,

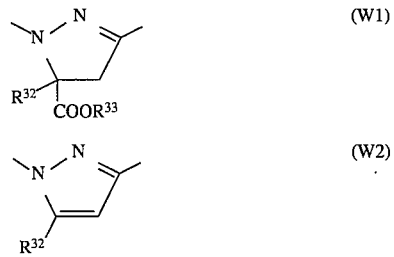

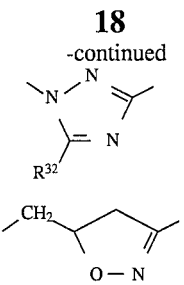

-continued $R^{32}$ is hydrogen, ($C_1$-$C_8$)alkyl, ($C_1$-$C_8$)haloalkyl, ($C_3$-$C_{12}$)cycloalkyl or optionally substituted phenyl and $R^{33}$ is hydrogen, ($C_1$-$C_8$)alkyl, ($C_1$-$C_8$)haloalkyl, ($C_1$-$C_4$)alkoxy($C_1$-$C_4$)alkyl, ($C_1$-$C_6$)hydroxyalkyl, ($C_3$-$C_{12}$)cycloalkyl or tri($C_1$-$C_4$)alkylsilyl.

2. An agent as claimed in claim 1, in which, in formula B1, $R^{31}$ is hydrogen, ($C_1$-$C_8$)alkyl or ($C_3$-$C_7$)cycloalkyl, where the above carbon-containing radicals are unsubstituted or mono- or polysubstituted by halogen or mono- or disubstituted by radicals selected from the group comprising hydroxyl, ($C_1$-$C_4$)alkoxy, ($C_1$-$C_4$)alkoxycarbonyl, ($C_2$-$C_6$)alkenyloxycarbonyl, ($C_2$-$C_6$)alkynyloxycarbonyl, 1-(hydroxyimino)($C_1$-$C_4$)alkyl, 1-[($C_1$-$C_4$)alkylimino]($C_1$-$C_4$)alkyl, 1-[($C_1$-$C_4$)alkoxyimino]($C_1$-$C_4$)alkyl and radicals of the formulae —$SiR'_3$, —O—N=$CR'_2$, —N=$CR'_2$ and —O—$NR'_2$ in which the R' radicals in said formulae independently of one another are hydrogen or ($C_1$-$C_4$)alkyl, or two of these radicals together are a ($C_4$-$C_5$)alkanediyl chain, $R^{32}$ is hydrogen, ($C_1$-$C_8$)alkyl, ($C_1$-$C_6$)haloalkyl, ($C_3$-$C_7$)cycloalkyl or phenyl and $R^{33}$ is hydrogen, ($C_1$-$C_8$)alkyl, ($C_1$-$C_8$)haloalkyl, ($C_1$-$C_4$alkoxy)($C_1$-$C_4$)alkyl, ($C_1$-$C_6$)hydroxyalkyl, ($C_3$-$C_7$)cycloalkyl or tri($C_1$-$C_4$)alkylsilyl.

3. An agent as claimed in claim 1, in which, in formula B1,

X' is hydrogen, halogen, nitro or ($C_1$-$C_4$)haloalkyl, n' is 1, 2 or 3,

Z' is a radical of the formula $OR^{31}$, $R^{31}$ is hydrogen, ($C_1$-$C_8$)alkyl or ($C_3$-$C_7$)cycloalkyl, where the above carbon-containing radicals are unsubstituted or mono- or polysubstituted, preferably up to trisubstituted, by identical or different halogen radicals or up to disubstituted by identical or different radicals selected from the group comprising hydroxyl, ($C_1$-$C_4$)alkoxy, ($C_1$-$C_4$)alkoxycarbonyl, ($C_2$-$C_6$)alkenyloxycarbonyl, ($C_2$-$C_6$)alkynyloxycarbonyl, 1-(hydroxyimino)($C_1$-$C_4$)alkyl, 1-[($C_1$-$C_4$)alkylimino]($C_1$-$C_4$)alkyl, 1-[($C_1$-$C_4$)alkoxyimino]($C_1$-$C_4$)alkyl and the radicals of the formulae —$SiR'_3$, —O—N=$R'_2$, —N=$CR'_2$ and —O—$NR'_2$, in which the radicals R' in said formulae independently of one another are hydrogen or ($C_1$-$C_4$)alkyl, or two of these radicals together are ($C_4$ or $C_5$)alkanediyl, $R^{32}$ is hydrogen, ($C_1$-$C_8$)alkyl, ($C_1$-$C_6$)haloalkyl, ($C_3$-$C_7$)cycloalkyl or phenyl and $R^{33}$ is hydrogen, ($C_1$-$C_8$)alkyl, ($C_1$-$C_8$)haloalkyl, ($C_1$-$C_4$)alkoxy($C_1$-$C_4$)alkyl, ($C_1$-$C_6$)hydroxyalkyl, ($C_3$-$C_7$)cycloalkyl or tri($C_1$-$C_4$)alkylsilyl.

4. An agent as claimed in claim 3, wherein in formula A

X is an oxygen atom,

Y is N or CH, $R^2$ and $R^3$ independently of one another are $(C_1-C_4)$alkyl, $(C_1-C_4)$alkoxy or $(C_1-C_4)$haloalkoxy, and $R^5$ is hydrogen, halogen, cyano, $(C_1-C_4)$alkyl, $(C_1-C_4)$alkoxy, $(C_1-C_4)$-haloalkyl or $(C_1-C_4)$haloalkoxy.

5. An agent as claimed in claim 4, wherein in formula A
$R^2$ and $R^3$ independently of one another are methyl or methoxy, and
$R^5$ is hydrogen.

6. An agent as claimed in claim 1, in which, in formula B2,
$X'$ is hydrogen, halogen or $(C_1-C_4)$haloalkyl,
$n'$ is 1, 2 or 3,
$Z'$ is a radical of the formula $OR^{31}$,
$R^*$ is $CH_2$ and
$R^{31}$ is hydrogen, $(C_1-C_8)$alkyl, $(C_1-C_8)$haloalkyl or $(C_1-C_4)$alkoxy$(C_1-C_4)$alkyl, 1-(hydroxyimino)$(C_1-C_4)$alkyl, 1-[$(C_1-C_4)$alkylimino]$(C_1-C_4)$alkyl, 1-[$(C_1-C_4)$alkoxyimino]$(C_1-C_4)$alkyl.

7. An agent as claimed in claim 1, which comprises a plurality of herbicidal active substances of the formula A.

8. An agent as claimed in claim 1, in which the ratio by weight of safener:herbicidal active substance is in the range of from 1:10 to 10:1.

9. An agent as claimed in claim 1, which comprises 0.1 to 99% by weight of at least one active substance of the formula B1 and/or B2 or of the herbicide/antidote active substance mixture A and B1 and/or B2, and 1 to 99.9% by weight of a solid or liquid additive, and 0 to 25% by weight of a surfactant.

10. An agent as claimed in claim 1 wherein the herbicidal substance of formula A is 2-(2-benzyloxycarbonylpyrid-3-yloxy)-4,6-dimethoxypyrimidine.

11. A herbicidal agent which contains
A) at least one herbicidal active substance from the group of the substituted pyrimidines and triazines of the formula A

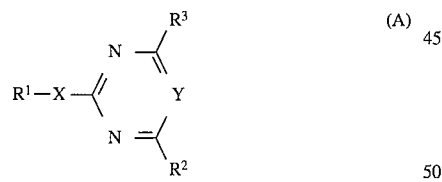

in which
X is an oxygen atom,
Y is N or CH,
$R^2$ and $R^3$ independently of one another are methyl or methoxy,
$R^1$ is a substituted aryl or heteroaryl radical of the formula

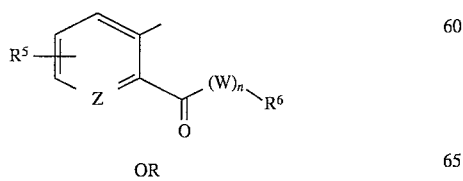

OR

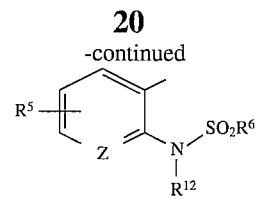

$n$ is 0 or 1,
W is $-O-$, $-NR^4-$, $-S-$, $-ON(R^{11})-$ or $-O-N=C(R^{11})-$,
Z is N, N—O or $CR^4$,
$R^4$ is hydrogen, halogen, $(C_1-C_2)$alkyl, $(C_1-C_2)$alkoxy, $(C_1-C_2)$haloalkyl or $(C_1-C_2)$haloalkoxy,
$R^5$ is hydrogen,
$R^6$ is hydrogen, $(C_1-C_4)$alkyl, $(C_2-C_4)$alkenyl, $(C_2-C_4)$alkynyl, alkali metal or 1 equivalent alkaline earth metal, alkylammonium, aryl, $CF_3$ or $(CHR^{13})_{m'}$, $CHR^7R^8$ where $m'$ is 0 or 1,
$R^7$ and $R^{13}$ independently of one another are hydrogen, $(C_1-C_4)$alkyl or $(C_1-C_4)$alkoxy,
$R^8$ is $(C_1-C_4)$alkoxycarbonyl, cyano, halogen, acetyl, pivaloyl, benzoyl, $(C_1-C_4)$alkoxy, aryloxy, haloacetoxy, methanesulfonyloxy, hydroxyl, $(C_1-C_4)$alkylmercapto, $(C_1-C_4)$alkylsulfonyl, arylmercapto, di-$(C_1-C_4)$alkylamino, pyridyl, aryl or $CONR^9R^{10}$,
$R^9$ and $R^{10}$ independently of one another are hydrogen, $(C_1-C_4)$alkyl, $(C_2-C_4)$alkenyl, aryl or benzyl,
$R^{11}$ is hydrogen or $(C_1-C_4)$alkyl or
$R^6$ and $R^{11}$ together are methylene, ethanediyl or propanediyl,
$R^{12}$ is hydrogen, alkyl or alkoxy and
aryl is phenyl or naphthyl, each of which is unsubstituted or mono- or disubstituted by radicals selected from the group comprising halogen, $(C_1-C_4)$alkyl, $(C_1-C_4)$alkoxy, phenoxy, nitro and $(C_1-C_4)$alkoxycarbonyl, or
$R^1$ is a radical of the formula

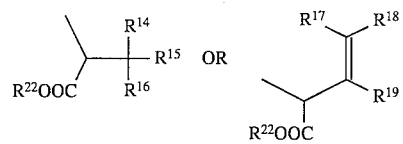

$R^{14}$ is hydrogen, halogen, halo $(C_1-C_4)$alkyl, $(C_1-C_4)$alkyl, cycloalkyl, $(C_1-C_4)$alkylmercapto$(C_1-C_4)$alkyl, hydroxy$(C_1-C_4)$alkyl, hydroxyl, cyano, aryloxy$(C_1-C_4)$alkyl, thienyl, aryl, dihydronaphthyl or

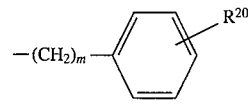

where aryl is as defined above,
$R^{20}$ is hydrogen, halogen, nitro, $(C_1-C_4)$alkyl, $(C_1-C_4)$alkoxy or $S(O)_pR^{21}$,
$R^{21}$ is alkyl,
$p$ is 0, 1 or 2,
$m$ is 0, 1 or 2,
$R^{15}$ and $R^{16}$ independently of one another are hydrogen or alkyl, or together with the carbon atom form a 3-, 4-, 5- or 6- membered cycloalkane ring in which a methylene group can be replaced by oxygen and which can be substituted by one or two alkyl groups, $R^{17}$ and $R^{18}$ independently of one another are hydrogen or $(C_1-C_4)$alkyl, $R^{19}$ is $(C_1-C_4)$alkyl or phenyl, or $R^{18}$ and $R^{19}$ are —$(CH_2)_l$— where l is 3 or 4 and which can be substituted by one or two alkyl groups, $R^{22}$ is hydrogen, $(C_1-C_4)$alkyl, $(C_1-C_4)$alkenyl, $(C_1-C_4)$alkynyl, phenyl, $(C_1-C_4)$alkylideneamino, $(C_1-C_4)$alkoxycarbonyl$(C_1-C_4)$alkyl, $(C_1-C_4)$alkoxy$(C_1-C_4)$alkyl, halo$(C_1-C_4)$alkyl, cycloalkyl, nitro-substituted phenylmercapto-$(C_1-C_4)$alkyl, halogen or benzyl which can be substituted by $(C_1-C_4)$alkyl or $(C_1-C_4)$alkoxy, or a salt thereof, and, B) 1-allyloxyprop-2-yl (5-chloro-8-quinolinoxy) acetate.

12. A herbicidal agent which comprises 2-(2-benzyloxycarbonyl-pyrid-3-yloxy)-4,6-dimethoxypyrimidine and 1-allyloxyprop-2-yl(5-chloro-8-quinolinoxy)acetate.

13. A herbicidal agent which comprises 2-(2-benzyloxycarbonyl-pyrid-3-yloxy)-4,6-dimethoxypyrimidine and ethyl 1-(2,4-dichlorophenyl)-5-(ethoxycarbonyl)-5-methyl-2-pyrazolin-3-carboxylate.

14. A method of protecting crop plants against phytotoxic secondary effects of herbicides, which comprises applying an effective amount of at least one safener compound of the formula B1 and/or B2 before, after or together with the herbicidal active substance, of the formula A, to the plants, seeds of plants or the area under cultivation, wherein the compounds of formula B1 and B2 and the herbicidal active substance of formula A are as defined in claim 1.

15. Method as claimed in claim 14, wherein the safener of the formula B1 and/or B2 is applied at an application rate of from 0.001 to 5 kg/ha of active ingredient and a ratio by weight of safener:herbicidal active substance in the range of from 1:10 to 10:1.

16. The method as claimed in claim 15, wherein the crop plants are cereal plants or corn plants.

* * * * *